United States Patent
von Campenhausen (10) Patent No.: US 11,191,898 B2
(45) Date of Patent: Dec. 7, 2021

(54) DRUG DELIVERY PUMP SYSTEM

(71) Applicant: Roche Diabetes Care, Inc., Indianapolis, IN (US)

(72) Inventor: Harald von Campenhausen, Mannheim (DE)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 121 days.

(21) Appl. No.: 16/347,869

(22) PCT Filed: Nov. 30, 2017

(86) PCT No.: PCT/EP2017/081057
§ 371 (c)(1),
(2) Date: May 7, 2019

(87) PCT Pub. No.: WO2018/100102
PCT Pub. Date: Jun. 7, 2018

(65) Prior Publication Data
US 2019/0275249 A1 Sep. 12, 2019

(30) Foreign Application Priority Data
Nov. 30, 2016 (EP) ..................................... 16201526

(51) Int. Cl.
*A61M 5/172* (2006.01)
*G16H 20/17* (2018.01)
(Continued)

(52) U.S. Cl.
CPC ........ *A61M 5/1723* (2013.01); *A61M 5/1456* (2013.01); *G16H 20/17* (2018.01);
(Continued)

(58) Field of Classification Search
CPC .............. A61M 5/1723; A61M 5/1456; A61M 5/14244; A61M 2005/14208;
(Continued)

(56) References Cited

U.S. PATENT DOCUMENTS

2002/0087113 A1  7/2002  Hartlaub
2003/0163223 A1*  8/2003  Blomquist .......... A61M 5/1723
                                                      700/282
(Continued)

FOREIGN PATENT DOCUMENTS

WO  WO 2010/029551 A2  3/2010
WO  WO-2010029551 A2 *  3/2010 ............. G16H 20/60

*Primary Examiner* — Bhisma Mehta
*Assistant Examiner* — Robert F Allen
(74) *Attorney, Agent, or Firm* — Woodard, Emhardt, Henry, Reeves & Wagner, LLP (57) ABSTRACT

The invention relates to a drug delivery system for a patient comprising an insulin delivery device (100), a user interface (101), a controller (109) comprising instructions and a user definable threshold criterion (114; 116) of a residual availability of a drug provided in a reservoir (102) of the drug delivery system, wherein executing of the instructions by the controller (109) causes the controller (109) to control the drug delivery system to determine the amount of the drug that is currently available to the patient and compare the determined amount with the threshold criterion (114; 116),
(Continued)

in response to the comparison, in case the determined amount is lower than or equal to the threshold criterion (114; 116), providing a signal to the patient via the user interface (101). The drug is insulin.

16 Claims, 3 Drawing Sheets

(51) Int. Cl.
*G16H 40/63* (2018.01)
*A61M 5/145* (2006.01)
*G16H 40/67* (2018.01)
*A61M 5/142* (2006.01)

(52) U.S. Cl.
CPC ......... *G16H 40/63* (2018.01); *A61M 5/14244* (2013.01); *A61M 2005/14208* (2013.01); *A61M 2205/183* (2013.01); *G16H 40/67* (2018.01)

(58) Field of Classification Search
CPC .... A61M 5/14566; A61M 2005/14252; A61M 2005/14268; A61M 2205/18; A61M 2205/183; G16H 20/17; G16H 40/63; G16H 40/67; A61B 5/0022; A61B 5/4839; A61B 5/6801; A61B 5/72; A61B 5/742; A61B 5/14532; A61B 5/7435; A61B 5/7475; A61B 5/0004
See application file for complete search history.

(56) References Cited

U.S. PATENT DOCUMENTS

| | | | |
|---|---|---|---|
| 2008/0033361 A1* | 2/2008 | Evans | A61M 5/172 604/151 |
| 2009/0209938 A1* | 8/2009 | Aalto-Setala | G16H 20/17 604/503 |
| 2010/0010646 A1* | 1/2010 | Drew | A61M 5/14276 700/86 |
| 2012/0072236 A1* | 3/2012 | Atkin | G16H 10/65 705/3 |
| 2016/0030683 A1* | 2/2016 | Taylor | A61M 5/32 604/151 |
| 2016/0066843 A1* | 3/2016 | Mensinger | A61B 5/0022 600/365 |
| 2020/0251210 A1* | 8/2020 | Skoda | H04L 67/025 |

* cited by examiner

DRUG DELIVERY PUMP SYSTEM

The invention relates to a drug delivery system, a controller, a method for operating a drug delivery system and a computer program product.

Drug delivery systems are medical devices that provide prescribed fluids to patients. For example, medications such as antibiotics, chemotherapy drugs and insulin are commonly delivered to patients via a drug delivery system. For example, WO 2015/073243 A1 discloses an infusion pump system that includes at least one reservoir having a reservoir volume, and an infusion pump including a pumping mechanism operably coupled to that at least one reservoir, including a memory and configured to control operation of the pumping mechanism, and a calculation module configured to determine at least one characteristic about the at least one reservoir.

It is an objective of the present invention to provide for an improved drug delivery system, a controller for the system, a method for operating such a drug delivery system and a computer program product.

The invention is described by the independent claims. Embodiments are described in the dependent claims.

Embodiments relate to a drug delivery system for a patient, preferably a diabetes patient, comprising a insulin delivery device, a user interface, a controller comprising instructions and a user definable threshold criterion of a residual availability of a drug provided in a reservoir of the drug delivery system, wherein executing of the instructions by the controller causes the controller to control the drug delivery system to:
 a) determine the amount of the drug that is currently available to the patient,
 b) compare the determined amount with the threshold criterion,
 c) in response to the comparison, in case the determined amount is lower than or equal to the threshold criterion, providing a signal to the patient via the user interface.

Embodiments may have the advantage that first of all the patient of the drug delivery system is actively informed by the device about the amount of drug that is currently available to the patient. However, in order to avoid an unnecessary bothering of the patient with reminders regarding the actually available amount of drug, the patient has the possibility to personally define a threshold criterion of a residual availability of the drug provided in the reservoir of the drug delivery system.

In an embodiment, the patient has the possibility to define or select the threshold criterion within a predefined range of threshold criteria that has a minimum lowest selectable or definable value. This may have the advantage that the patient does not expose herself or himself to danger because the threshold was set too low (and thus the time to react to a depletion of the available amount of drug is too short).

The "threshold criterion" is understood as one or more threshold values regarding the residual availability of the drug in the reservoir and/or the amount of the drug that is currently available in the reservoir. The residual availability and the amount of the drug that is currently available is specified using a measurement unit. In a simple example, the threshold value may be a number "5" and the measurement unit may be "days of use until the drug is used up", which means that in case the amount of the drug that is currently available to the patient will last for 5 days or less, the signal will be provided to the patient via the user interface.

In an embodiment a patient may individually select his or her own threshold criterion. This may increase the probability that signals provided via the user interface to the patient are treated seriously by the patient and not ignored because the signal is provided by the drug delivery system for example at a certain level of availability of the drug for which the patient is of the opinion that a reminder is neither necessary nor helpful.

Thus, embodiments of the invention may consider that patients may have individual demands regarding the necessity to be informed about the remaining amount of the drug that is currently available in the reservoir. In a practical example, a patient or patient that requires large amounts of the drug each day may have the desire to be informed at a larger remaining drug level in the reservoir of the drug delivery system compared to a patient who only occasionally makes use of the drug delivery system or who requires smaller amount of the drug each day. In a further example, in case of a journey to locations with limited availability of the drug for replenishment of the reservoir, the patient may have the desire to be informed at a much larger remaining level of drug in the reservoir compared to the situation in which the patient is at home or at a location with abundant sources for replenishment of the reservoir with drug such as in a big city with multiple drug stores at hand.

Thus, the above described embodiment may permit the patient to define the remaining amount of the drug in the reservoir at which the signal is provided to him via the user interface. Alternatively or additionally, the signal may also be provided to third parties like doctors, caregivers, family members or other people that may be definable by the patient.

As described above, a drug is understood as any kind of medication such as antibiotics, chemotherapy drugs, pain relievers, etc., preferably as insulin and/or glucagon.

In accordance with an embodiment of the invention, the amount of the drug that is currently available to the patient is any one of:
 the amount of the drug that is currently available in the reservoir,
 the amount of the drug that is stored outside the reservoir at the patient and that has been electronically assigned to the drug delivery system.

The phrase 'stored outside the reservoir at the patient' may for example be understood as stored at a location that is not the drug delivery system but a location to which the patient has preferably immediate access. For example, a patient may have already obtained one or more further replacement cartridges of the drug for replenishment of the reservoir. In this case, the patient may assign or register these drugs that are now stored outside the reservoir to the drug delivery system in an electronic manner. For example, a globally unique identifier that is assigned to each individual drug cartridge may be communicated to the drug delivery system. From this identifier the drug delivery system will understand that additional drugs are immediately available and in close vicinity to the patient for replenishment of the reservoir if necessary. Alternatively, the patient or another person like a health care provider may manually enter the amount of drug that are now stored outside the reservoir at the patient in the drug delivery system.

In accordance with a further embodiment, the amount of the drug that is currently available in the reservoir and the amount of the drug that is stored outside the reservoir and assigned to the drug delivery system may both be considered, however with different weightings. The amount of the drug that is currently available in the reservoir may be more heavily weighted than the amount of drug that is stored outside the reservoir such that it may be ensured that in case the drug in the reservoir is going to be exhausted the patient is nevertheless informed in time via the signal about this diminishing drug. Depending on the availability or non-availability of the 'replacement drugs' stored outside the reservoir, the level of the amount of drug that is currently available in the reservoir and that triggers the signal provision to the patient may be set lower or accordingly higher. All this may be either patient-adjustable or automatic.

In accordance with an embodiment of the invention, the residual availability of the drug in the reservoir and/or the amount of the drug that is currently available in the reservoir is specified using any one measurement unit of:
a) a remaining estimated time period of use until the drug is used up,
b) a remaining amount of individual boluses for the patient until the drug is used up,
c) a remaining absolute amount of the drug,
d) a remaining relative amount of the drug in the reservoir in relation to an amount of the drug that is maximally available in the reservoir.

The user definable threshold criterion (114; 116) of a residual availability of a drug provided in a reservoir (102) of the drug delivery system will be based on the measurement unit used to specify the amount of the drug that is currently available in the reservoir. For example if the measurement unit used to specify the amount of the drug that is currently available in the reservoir is the remaining estimated time period of use until the drug is used up, the user defined threshold criterion will be defined in relation to the remaining estimated time period of use until the drug is used up. This logic applies mutatis mutandis to the other measurement units mentioned in the preceding paragraph.

If the measurement unit used to specify the amount of the drug that is currently available in the reservoir is the remaining estimated time period of use until the drug is used up, the user defined threshold criterion is preferably a time of up to 2 days, up to 1 day, up to 10 hours, up to 5 hours, up to 3 hours, up to 1 hour, up to 30 minutes or up to 10 minutes.

If the measurement unit used to specify the amount of the drug that is currently available in the reservoir is the remaining absolute amount of the drug, the user defined threshold criterion is preferably an amount of up to 5 units, up to 10 units, up to 20 units, up to 30 units, up to 40 units, up 50 units, up to 60 units, up to 70 units, up to 80 units of the drug.

If the measurement unit used to specify the amount of the drug that is currently available in the reservoir is the remaining relative amount of the drug in the reservoir in relation to an amount of the drug that is maximally available in the reservoir, the user defined threshold criterion is preferably an amount corresponding to up to 5%, up to 10%, up to 15%, up to 20%, up to 25%, up to 30%, up to 40%, up to 50%, up to 60%, up to 70% of the amount of the drug that is maximally available in the reservoir.

This threshold criterion may be adapted to the needs of the user and may thus help to attract the patient's attention to the signal that is provided to the patient via the user interface. To tailor the signals to the patient's needs, for example, a patient that requires many times a day a rather small bolus of the drug may prefer to specify his threshold using the measurement unit 'remaining estimated time period of use until the drug is used up' rather than the measurement unit of 'remaining amount of individual boluses for the patient until the drug is used up'. For this patient, it may be more intuitively understood what it means that the drug in the reservoir will be used up within the next 24 hours rather than the measurement unit that after the next subsequent 35 boluses the drug available in the reservoir will be used up.

In another embodiment the drug delivery system may also be adapted to set different threshold criteria and assign each threshold criterion to a dedicated type of signal. Further, in another embodiment the drug delivery system may also be adapted to set the different threshold criteria with respect to different measurement units. For example, one threshold criterion would be "10% of residual amount of drug left" and a further threshold criterion would be "only 3 boluses left until depletion of the reservoir".

In accordance with an embodiment of the invention, the remaining time period of use and/or the remaining amount of individual boluses until the drug that is currently available in the reservoir is used up is determined based on any one of the following:
an estimated future physical behavior of the patient,
an estimated future carbohydrate consumption of the patient (e.g. based on an average of carbohydrates the patient consumes over certain period of time like over a day which could be determined by tracking the carbohydrate consumption over a longer period of time),
estimated future bolus doses of the drug required by the patient,
an average bolus dose of the drug for a time period,
a blood glucose measurement pattern obtained for a time period immediately preceding the time point for which the currently available amount of drug is determined, and
the remaining time period of guaranteed stability of the drug.

In a preferred embodiment of the invention the remaining estimated time period of use until the drug is used up (T) is determined based on the residual amount of the drug available in the reservoir (Vres), the amount of drug administered per time (D=amount of drug administered per time, e.g. in U/t), e.g. as follows: T=Vres/D. The time period may be given in any suitable time period like days, hours, or weeks. Methods to determine the residual amount of the drug available in the reservoir are implemented in infusion pumps available on the market and generally known in the art. In one embodiment the amount of drug administered per time can also be readily determined by various methods including a) calculation based on empirical data on the amount of drug administered to the patient over a monitored period of time, or b) data entry on the amount of drug administered per time by the patient or a user into the drug delivery system. In one embodiment the monitored time period is a period of up to 1 week, up to 2 weeks or up to 3 weeks. The size of this amount of drug administered per time is preferably specified in units of the drug per time. Preferably, the calculation of T also takes into account that T is not larger than the remaining time period of guaranteed stability of the drug.

In a preferred embodiment of the invention the remaining amount of individual boluses for the patient until the drug that is used up (B) is determined based on the residual amount of the drug available in the reservoir (Vres), the average size of the boluses given by the patient (Ab), e.g. as follows: B=Vres/Ab. In the event the patient not only administers individual boluses but also receives regular basal rate boluses the calculation may further take into account a safety margin (SMt) of the amount of drug to be administered at the basal rate over a certain safety time period of e.g. up to 1 day, up to 2 days, up to 3 days, up to 4 days or up 5 days. In this embodiment the safety margin may be subtracted to yield a safety margin corrected value B. For example, if Vres is 50 Units of insulin, Ab is 2 units of insulin per bolus and the SMt of the drug administered over a period of 1 day is 20 units of insulin then B=(Vres/Ab)−SMt=50/2−20=5 boluses. In one embodiment the average size of the boluses given by the patient can also be readily determined by various methods including a) calculation based on empirical data on the size of drug boluses administered to the patient over a monitored period of time, or b) data entry on the average size of the boluses by the patient or a user into the drug delivery system. The size of this average bolus is preferably specified in units of the drug.

Methods to determine the residual amount of the drug available in the reservoir are implemented in infusion pumps available on the market and generally known in the art. In one embodiment the amount of drug administered per time can also be readily determined by various methods including a) calculation based on empirical data on the amount of drug administered to the patient over a monitored period of time, or b) data entry on the amount of drug administered per time by the patient or a user into the drug delivery system. In one embodiment the monitored time period is a period of up to 1 week, up to 2 weeks or up to 3 weeks.

In one embodiment the physical behavior, either past and/or future activity of the patient is also taken into account as a parameter to determine the remaining estimated time period of use until the drug is used up or the remaining amount of individual boluses for the patient until the drug that is used up.

A 'physical behavior' of the patient may comprise a physical activity like a sport activity of the patient. Further, it may comprise meals of the patient, wherein the meals may be provided either in terms of uptake of calories, carbohydrate units, bread units or by indication of the ingredients of the meal and the amount of the meal that is taken up.

Further, the average bolus dose may be considering basal boluses, as well as individual bolus injections.

Based on a calculation that integrates at least one of the above parameters it is possible to predict more accurately if the determined amount of the drug that is currently available in the reservoir meets the threshold criterion set by the patient and/or to predict when the threshold level will be reached. For example, if the patient decided that he or she wants to provide a threshold criterion with the measurement unit of a remaining time period of use until the drug is used up, for one patient a remaining reservoir level of 25% may correspond to a rather large time period of use until the drug is used up compared to a patient which requires the drug in larger amounts on a regular basis, such that this 25% level corresponds already a critical level which requires immediate attention by the patient. Thus, by allowing the patient or a user to set the above threshold criterion the drug delivery system can be tailored to the individual patient's needs and also allows for adapting the system to patient's needs that may change over time.

In accordance with an embodiment of the invention, the physical behavior of the patient may be estimated using a retrospective analysis of a previous physical behavior of the patient accounting for reoccurring physical events of the patient and/or the future bolus doses may be estimated using a retrospective analysis of previous bolus dosages of the drug and accounting for reoccurring bolus doses of the patient. Physical events are commonly tracked in log books used by diabetes patients which are using drug delivery systems like insulin pumps. Based on this estimation it is then possible to predict the impact on the physical behavior on the drug consumption, e.g. so as to determine if or even predict when the threshold criterion is or will be reached. For example, a patient may regularly work out in a gym every other day and based on past monitoring the patient determined that on work out days the average amount administered insulin is 10 units below the amount administered on days without workout. Such information can then be included into the calculation of the remaining estimated time period of use until the drug is used up and the remaining amount of individual boluses for the patient until the drug that is used up, respectively.

A predication may be made using a retrospective analysis of reoccurring physical events or bolus doses that happened in the past for estimating the future physical behavior or the future bolus doses. Additionally or alternatively the drug delivery system may have access to a personal calendar of the patient which indicates certain future events of physical behavior of the patient which can then also be taken into account to determine if or even predict when the threshold criterion is or will be reached.

The retrospective analysis may comprise a clustering of the reoccurring physical events and/or boluses according to same time periods like days, hours, months. Thus, by clustering historical data regarding the past physical behavior of the patient or the past bolus doses that were provided to the patient, it may be possible to more accurately predict a future physical behavior or bolus dose required by the patient. In an example, the retrospective analysis may determine that in 90% of the past days, the patient had breakfast at 8 o'clock and took a walk at 8:30, such that from the retrospective analysis of this information it is estimated that for the next days the patient behavior will be similar. Therefore, expected bolus doses in the time period between 8 o'clock and 9 o'clock may be considered for determining the remaining time period of use and/or the remaining amount of individual boluses until the drug that is currently available in the reservoir is used up.

By considering the blood glucose measurement pattern obtained for a time period immediately preceding the time point for which the currently available amount of drug is determined, it may be possible to predict if the patient will require more or less amounts of the drug in the future time. For example in case of a pattern that indicates that the required amount of drug was continuously increasing within a past time period, this increase may be extrapolated and it may be predicted that in the upcoming days the amount of drug that is required by the patient may also be steadily increasing. This may thus permit for a more accurate prediction of the remaining time period of use or remaining amount of individual boluses until the drug available in the reservoir is used up.

In accordance with an embodiment of the invention, the controller is comprising a memory and a processor, the memory comprising the instructions and the user definable threshold criterion.

In accordance with an embodiment of the invention, the controller is comprised by anyone of the following:
  the drug delivery system, and
  a remote control spatially separated from the drug delivery system, the remote control being adapted to enable the user of the drug delivery system to set the user definable threshold criterion.

Thus, the controller may be any remote control device that is spatially separated from the drug delivery system and controls the operation of the drug delivery system by for example providing control commands to the drug delivery system regarding the time and duration of providing boluses to the patient. The remote control may be wired or wirelessly connected to the drug delivery system using for example Bluetooth, Wlan, NFC. The remote control may be integrated for example as hardware module or as software module in a mobile telecommunication device like a smart phone, tablet PC, PC, or a smart watch.

Generally, the controller may comprise a transmission unit to send and receive information. For example, information may be received from a blood glucose sensor measurement device meter measuring or a continuous glucose sensor measurement device measuring glucose preferably in a bodily fluid of blood or interstitial fluid. Further information may be received from any medical device or from a mobile telecommunication device of a user (e.g. calendar entries from that device).

In accordance with an embodiment of the invention, executing of the instructions by the controller further causes the controller to control the drug delivery system to dynamically adjust the threshold criterion based on the current location of the patient and/or a future location of the patient where the patient will be located in a future time period, wherein the dynamical adjusting is taking into account the spatial availability of a drug at said location for replenishment of the reservoir.

As already mentioned above, in case the drug delivery system has the information that in the next days the patient will be in a special location, for example a certain country or city, where a possible supply of the patient with additional drugs is rather difficult, the drug delivery system may therefore dynamically adjust the threshold criterion in accordance with the local drug supply situation. The location information and/or the information on the local supply situation can, e.g. be entered by the patient or it can be determined based on information and GPS data retrieved by the drug delivery system. As a result the patient can be informed at an earlier time point about the necessity to obtain further drugs in the event there is limited availability of drugs at the location where the patient currently resides or in the near future will reside.

In accordance with an embodiment of the invention, executing of the instructions by the controller further causes the controller to control the drug delivery system to dynamically adjust the threshold criterion of a residual availability of a drug provided in a reservoir based on a current time point, the dynamical adjustment taking into account a temporal availability of a drug for replenishment of the reservoir with respect to said current time point. Similarly as described with respect to the spatial availability of the drug, this may ensure that the patient is not at risk of experiencing a situation in which additional drugs for replenishment of the reservoir are not available in due time after the patient has obtained the signal from the drug delivery system via the user interface, even though under 'normal circumstances' availability of the drug in due time for replenishment would not have imposed any problem. A practical example would be a threshold criterion that would have been set to 'one day of residual availability of the drug provided in a reservoir until drug is used up'. In case the patient is informed on a Monday this would be no problem for the patient because he or she could easily go to a shop on Monday afternoon or Tuesday to get additional drugs for replenishment of the reservoir. However, this would impose a serious problem to the patient in case he would be informed about reaching of the threshold value on a Sunday where in many countries many pharmacies are closed.

Thus, by adapting the drug delivery system to be able to dynamically adjust it may be ensured that the patient is not running into health problems due to non-availability of replacement drugs, even though under 'normal circumstances' the patient set threshold value was reasonable and sufficient for the patient.

In accordance with an embodiment of the invention, the user interface is for example a graphical user interface, an acoustical interface, a haptic interface or an over-the-air interface. A graphical user interface may be a graphical user interface which has a high resolution, low resolution or it may even comprise only a set of LEDs or even only one LED. In case of an acoustical interface, this may be a loudspeaker. A haptic interface may be any means which provides a haptic feedback to the patient, for example via certain vibrations or vibration patterns of the drug delivery system. An over-the-air interface may be a Bluetooth, infrared, wireless LAN, or even a mobile telecommunication interface.

In accordance with an embodiment of the invention, the signal provided to the patient via the user interface is a vibration or acoustic signal or a visual signal such as an image, an icon or message on the display, a message, e.g. an SMS, an email, a notification window on a mobile telecommunication device or a social platform message or a web messenger message. This may have the advantage that the patient is informed about the depletion of the drug in his drug delivery system in a convenient manner either on his computer or on his mobile telecommunication device, like for example his mobile phone or tablet PC.

In accordance with an embodiment of the invention, the user definable threshold criterion comprises a first threshold value and a second threshold value, wherein executing of the instructions by the controller causes the controller to control the drug delivery system to:
  detecting in response to the provision of the signal to the patient via the user interface the reception of a snooze command from the patient,
  in response to the detection of the reception of the snooze command, repeating steps a) to c) with the user definable threshold criterion being the second threshold value.

In the above embodiment, the comparison of the determined amount with the threshold criterion is first made by comparing the determined amount with the first threshold value. This comparison is used to provide the signal. If the user provides the snooze command, then the steps a)-c) as describe above are performed again. When steps a)-c) are performed again the comparison between the determined amount with the threshold criterion is them made with the second threshold value.

The first threshold and the second threshold are both equivalent. Both are values with can be compared to the determined amount. In some examples, the first threshold and the second threshold can be considered to be residual amounts of the drug in the reservoir.

This may have the advantage that the patient is given the possibility to postpone the replenishment of the drug or the refilling of the reservoir with a new drug in a convenient manner. The snooze command may be entered by pressing a certain button or button combination on the drug delivery system or by communicating a certain command via a mobile telecommunication device or a computer to the drug delivery system. Thus, it may be avoided that by accidentally dismissing the signal provided to the patient via the user interface the provision of the signal may be forgotten by the patient. Thus, the snooze command may permit the patient to be reminded again about the necessity to refill the reservoir or to replace the reservoir with a new one and thus conveniently provides a possibility to ensure that the health status of the patient is not negatively influenced due to accidental non-availability of the drug in the reservoir.

In accordance with an embodiment of the invention, the controller further comprises a user non-adjustable reserve threshold value, wherein executing of the instructions by the controller further causes the controller to control the drug delivery system to provide a signal as a dedicated warning signal to the patient via the user interface in case the determined amount is lower than or equal to the reserve threshold value. This may have the advantage that a situation is avoided in which for example due to many snooze commands from the patient or inappropriately defined threshold criterions the drug provided in the reservoir is completely used up and the patient may notice this problem at a too late time point. Therefore, by means of this non-adjustable reserve threshold value it is guaranteed that at a certain minimum level of the drug or a certain minimum remaining time period of use until the drug is used up or a certain minimum amount of individual boluses that are available until the drug is used up, the patient is warned that without any further action from his side he or she soon may run into health problems due to lack of any further drug available in the reservoir. The non-adjustable reserve threshold value could either be set during production of the system or set by a user different from the patient, preferably by a caregiver or a healthcare professional. To ensure that only certain users are able to set or amend the non-adjustable reserve threshold value, access to the modification of these settings could be restricted, e.g. by password protection, etc.

In accordance with an embodiment of the invention, executing of the instructions by the controller further causes the controller to control the drug delivery system to deactivate the dedicated warning signal upon detection of the drug in the reservoir above a minimum reservoir level. Preferably, the only possibility to deactivate the warning signal is by either turning off the drug delivery system or by refilling the reservoir or replacing the reservoir with a new reservoir such that the amount of drug in the reservoir is above the minimum reservoir level. Thus, any accidental dismissing of the warning signal may be avoided.

In accordance with an embodiment of the invention, executing of the instructions by the controller further causes the controller to control the drug delivery system to provide a warning message to a predefined user device, the warning message comprising identifying information concerning any one of:

the drug delivery system, the patient of the drug delivery system, the determined amount.

This may be additionally performed in case the determined amount is lower than or equal to the reserve threshold value.

This may have the advantage that a third party can be informed about the problematic situation regarding the depletion of the drug in the reservoir such that a third party action can still be initiated in due time. The predefined user device may be for example a user device of a medical doctor or a care giver. The predefined user device may be a computer, a mobile phone, a telefax machine or any device which can be selectively addressed by the drug delivery system. Communication between the drug delivery system and the predefined user device may be again performed via an over-the-air interface.

The warning message may be an email, an SMS, a social platform message, a web messenger message or any other message which permits the user of the predefined user device to identify the drug delivery system or the owner of the drug delivery system or a contact information regarding the patient and thus permits to initiate any counteractions to compensate for the depletion of the drug in the reservoir. For example, a medical doctor may call the patient of the drug delivery system via telephone and discuss with him or her the problem that the drug remaining in his drug delivery system is at a critical level. In another example, a care giver may directly drive to the patient (user) of the drug delivery system and provide support with the replenishment of the reservoir.

In another embodiment of the invention the entry and setting of the user definable threshold criterion of a residual availability of a drug provided in a reservoir of the drug delivery system is also restricted as described for the non-adjustable reserve threshold value.

In accordance with an embodiment of the invention, the system is comprising the reservoir and a drug outlet, the system being adapted for supplying the drug to the patient by pressing the liquid drug through the drug outlet In another embodiment, the drug is insulin.

In another embodiment, the insulin delivery device is a pump delivery device comprising a pump.

In another embodiment, the insulin delivery device is an insulin pen. In this embodiment, the insulin pen may be constructed with additional electronics and/or sensors. The insulin pen may for example incorporate the user interface and/or controller into the insulin pen. Alternatively, the insulin pen may have a wired or wireless means of communicating with the user interface and/or controller. For example, a Bluetooth or Wi-Fi connection may be provided between the insulin pen and the user interface and/or controller.

In one example, the insulin pen comprises electronics for determining when the insulin pen has been filled and then calculating the number of times the insulin pen has been used to determine the amount of insulin currently available to the patient. Alternatively, the insulin pen may send a signal to the controller via a wireless connection (as mentioned above) and the controller may count the number of times the insulin pen has been used to determine the amount of insulin currently available to the patient.

In another example, the insulin pen incorporates a sensor for measuring the amount of insulin available to the patient. The insulin pen may provide a measurement of the amount of insulin available to the controller. If the controller is integrated into the insulin pen than this measurement may be provided via a wired means. If the controller is external to the insulin pen then the measurement may be provided to the controller via a wireless connection as was mentioned above.

In another aspect, the invention relates to a method for operating a drug delivery system comprising a insulin delivery device with a pump, a user interface and a controller comprising a threshold criterion of a residual availability of a drug provided in a reservoir of the drug delivery system, the threshold criterion being definable by a patient of the drug delivery system, the method comprising by the drug delivery system:

a) determining the amount of the drug that is currently available to the patient, b) comparing the determined amount with the threshold criterion, c) in response to the comparison in case the determined amount is lower than or equal to the threshold criterion providing a signal to the patient via the user interface.

In another aspect, the invention relates to a computer program product comprising computer-executable instructions to perform the method as described above.

It is understood that one or more of the aforementioned embodiments of the invention may be combined as long as the combined embodiments are not mutually exclusive.

References to an "insulin delivery device" herein may be replaced with "pump delivery device."

References to an "drug delivery system" herein may be replaced with "drug delivery pump system."

BRIEF DESCRIPTION OF THE DRAWINGS

In the following, some preferred embodiments of the invention are described in greater detail by way of example only, making reference to the drawings in which.

In the following, similar elements are denoted by the same reference numerals.

Figure 1:
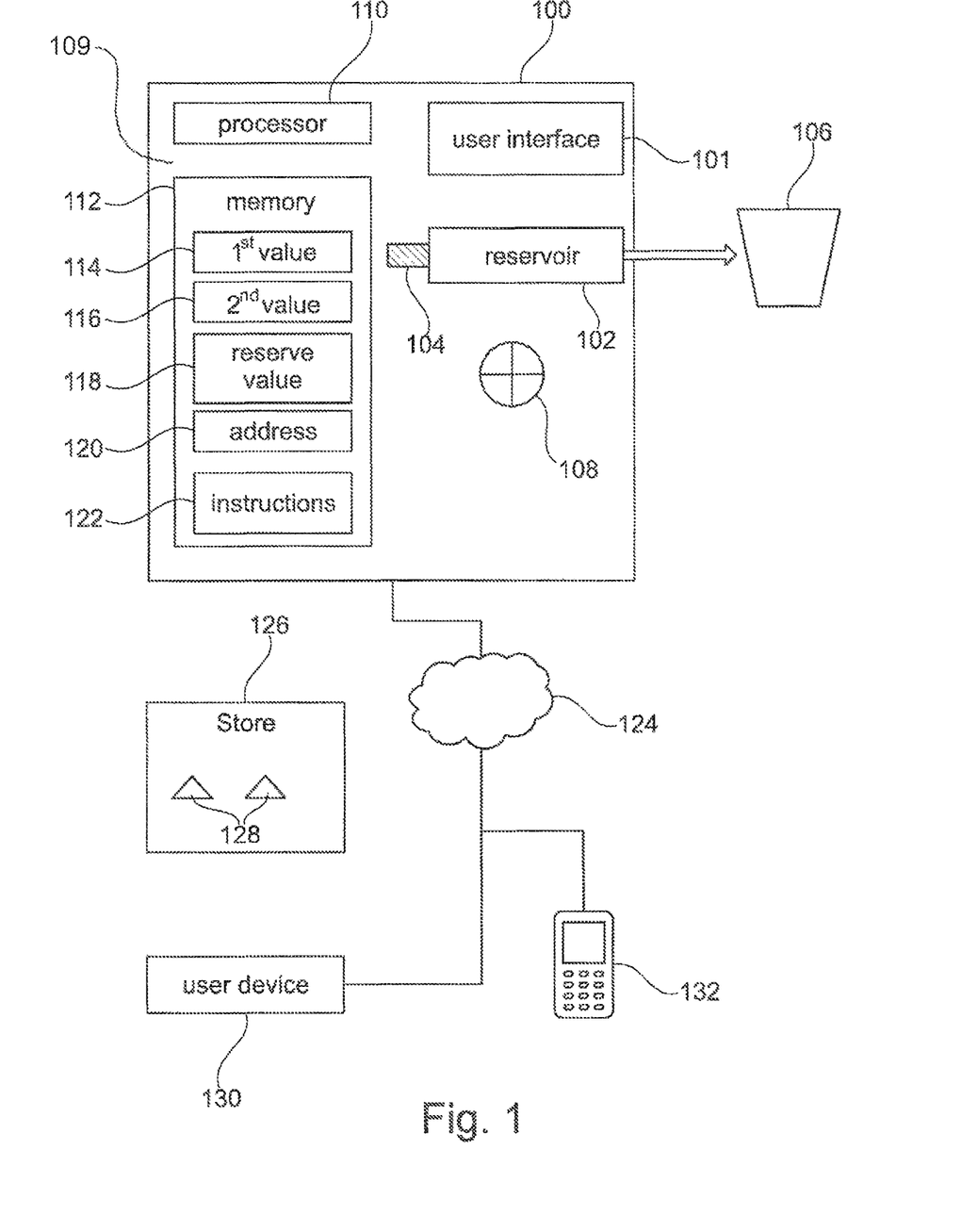
FIG. 1 is a block diagram of a drug delivery system.

FIG. 1 is a block diagram illustrating a drug delivery system comprising an insulin delivery device 100 used to provide a drug like insulin to a patient of the insulin delivery device 100. The drug contained in the reservoir 102 of the device 100 is fed via a pump 104 into the infusion tube of the infusion set 106 in order to be administered subcutaneously to the patient.

The insulin delivery device 100 further comprises a processor and a memory 112, the memory 112 comprising computer-executable instructions 122 which control the device 100 to perform its function of feeding the drug from the reservoir 102 to the infusion set 106.

In the following it is assumed without restriction to generality that the insulin delivery device 100 comprises a controller 109 built up from the memory 112 and the processor 110. However, it will be understood that this controller may also be located spatially separated from the drug delivery system 100 in an external remote control, like for example the mobile phone 132. In this latter case, the insulin delivery device 100 comprises a receiver which receives control commands from the remote control in order to carry out the feeding of the drug to the infusion set 106.

Further, the instructions 122 are adapted to inform a patient of the device 100 via the user interface 101 about the fact that the amount of the drug that is currently available in the reservoir 102 is smaller or equal to a threshold criterion that is user definable. The threshold criterion may comprise a first value 114 and a second value 116 which may both be stored in the memory 112. The memory 112 may further comprise a reserve value 118 which purpose will be described later. An address 120 of a care giver which address may also be user or patient-defined is also stored in the memory 112. While the first value 114 and the second value 116 are user definable, the reserve value 118 is a fixed value which preferably cannot be changed by the patient.

The user interface 101 may for example be a graphical user interface with a multitude of pixels which is able to display textual or pictorial information to the patient.

Finally, the device 100 may also comprise a sensor 108 like a GPS sensor which is able to detect the actual spatial location of the device 100.

The device 100 may be able to communicate via a network 124 like the wireless, cable or the internet with other devices like for example a mobile phone 132 of the patient or another medical device. Further, via the address 120 the device 100 is able to send a warning message via the network 124 towards the user device 130. Thus, the user device 130 is a device of the above mentioned care giver of the patient of the insulin delivery device 100.

Figure 4:
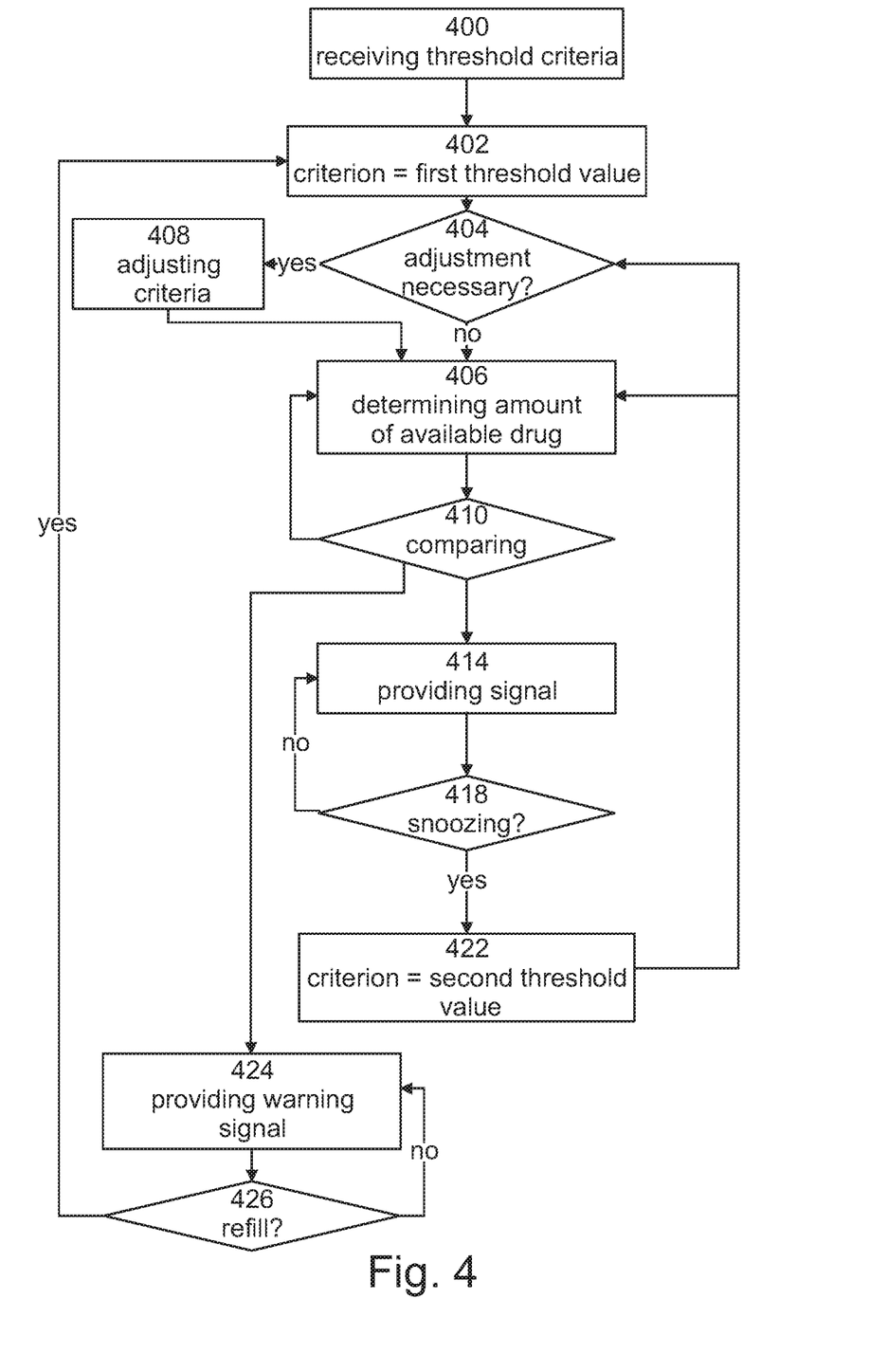
FIG. 4 is a flowchart illustrating a method of operating a drug delivery system.

In combination with FIG. 4 an exemplary operation of the drug delivery system 10 comprising the insulin delivery device 100 will be described in the following. It is assumed that with a first initialization and personalization of the insulin delivery device 100 to its patient, the patient is entering in block 400 certain threshold criteria, like the first and the second threshold value. Only for exemplary purposes it is assumed that the first and the second value both indicate a remaining time until the drug available in the reservoir will supposedly be used up. For example, the first value may correspond to 24 hours and the second value may correspond to 12 hours. Further, the reserve value 118 which is not patient-adjustable may be three hours.

After having received the threshold criteria in block 400, in block 402 the device 100 sets via its instructions 122 the first threshold value as the relevant criterion for assessment if a signal should be indicated to the patient via the user interface 101. Subsequent blocks 404 and 408 are optional and will be discussed later on. Therefore, in the following it is assumed that block 406 follows after block 402, wherein in block 406 the device 100 determines the amount of drug available for example in the reservoir 102. Additionally, the device 100 may also consider the amount of drug that is stored outside the reservoir 102 at the patient and that has been previously electronically assigned to the insulin delivery device. Thus, the device is aware of spare drugs that may replace the drug or fill up the reservoir with new drugs.

Thereupon, in decision block 410 the amount of the drug determined in block 406 is compared with the first threshold value. Comparison may for example mean that the device is checking the average amount of drug that is used within a certain time period, for example per hour. Based thereon, from the total available amount of drugs the device can calculate the total time that is remaining until the drug is completely used up. In case the determined amount is lower than or equal to the threshold criterion, a respective signal is provided to the patient via the user interface 101 in block 414. For example, a text message may appear on the user interface 101 informing the patient about the fact that the level in the reservoir has reached a limit at which the remaining drug will only last for less than 24 hours (first value 114).

Optionally, the device 100 may automatically add a respective reminder event indicating the necessity to refill or replenish the reservoir to a calendar of the patient's mobile phone 132.

In subsequent block 418 the device determines if the patient is providing a snoozing command to the device. In case no command is received, the message may either be continuously provided to the patient via the user interface, or after a certain time interval like for example five minutes the patient is reminded again by again providing the signal to the patient via the user interface. However, this may strongly depend on the type of user interface. For example, in case of an EPD (electronic paper display) due to the nature of the EPD an extra refreshment of the signal, i.e. of the text message is not necessary, whereas in case of a haptic signal like either a vibration of the device this vibration may be repeated in a regular manner. In case of a normal non-static display like an LCD display, the text message may appear in a blinking fashion thus saving energy of the LCD display since the message is not permanently displayed thereon.

In case in block 418 the reception of a snoozing command is detected by the device 100, the method continues with block 422. In block 422, due to the reception of the snooze command the criterion that is used for a subsequent comparison of the determined amount with the threshold criterion is set to be the second threshold value 116, and the method then continues in block 406. In other words, in block 422 the threshold criterion is changed to the second threshold value and thereupon, the above described procedure is repeated. As a result, in the present example the next signal that is provided to the patient will be the signal informing the patient that the level of drug in the reservoir has reached a level that permits to only use the device for a remaining time of 12 hours.

As a safety mechanism in decision block 410 the determined amount of available drug may also be compared with the reserve value level 118. In case it turns out that the determined amount is lower than or equal to the reserve threshold value level, the method does not continue from block 410 to block 414 with the 'normal' providing of the signal, but the method continues with block 424. Block 424 and subsequent block 426 are optional.

In block 424, both, a certain warning signal is provided to the patient via his user interface and additionally a warning signal or a dedicated warning message may be provided to a care giver of the patient of the drug delivery system 100. For example, the reserve threshold value 118 which indicates, that the amount of left drug in the reservoir 102 will only last for the next three hours is so critical, that a care giver of the patient is immediately informed via the respective signal in block 424 and is thus able to take respective counter action in due time. This may be necessary especially if the patient of the device 100 is an elderly person that does not have the mental capacity to react in a quick manner to this serious situation.

In order to contact the care giver, the warning message is provided to the address 120 that is stored in the memory 122. For example, an SMS message is sent via an over-the-air interface from the device 100 to the user device 130 of the care giver.

Preferably, the warning signal that is provided to the user interface 101 can only be dismissed or turned off in case of a detection of the drug in the reservoir above a minimum reservoir level. The patient may accomplish this by either refilling the reservoir with a new drug or by replacing the reservoir with a replacement reservoir 128 from his store 126.

Preferably, the first threshold value and the second threshold value or in general the threshold criterion are based on the residual amount of drug that is currently available in the reservoir 102. In other embodiments, the first threshold value and the second threshold value or in general the threshold criterion may not only be based on the residual amount of drug that is currently available in the reservoir 102 but instead, the device 100 may also take into account the amount of drug in the replacement reservoirs 128 of his or her store 126 when determining in block 406 the amount of available drug. For example, even though the residual amount of drug currently available in the reservoir may only last for the next 24 hours, the total amount of drug available to the patient may be enough to provide the patient with the drug for 3 days. For that reason, the patient may not have to be bothered with a signal informing him about the necessity to refill the reservoir within the next 24 hours since he already has the drug available for replenishment of the reservoir. In such instances, the amount of available drug in the reservoir may be only weighted with a weighting factor of 60% and the amount of drug that is available in the personal store of the patient may also be weighted with a weighting of 40%.

In a practical example, this may result in the following considering the first threshold of 24 hours and a weighting ratio of 60/40:

| Residual Drug in reservoir lasting for | Drug in store lasting for | Adjusted amount | Action necessary? |
|---|---|---|---|
| 48 hrs | 48 hrs | 48 hrs | No |
| 24 hrs | 48 hrs | 33.6 hrs | No |
| 12 hrs | 48 hrs | 26.4 hrs | No |
| 6 hrs | 48 hrs | 22.8 hrs | Yes |

Thus, instead of informing the patient about running out of the drug in case the drug in the reservoir is only presumably lasting for the next 24 hours, the patient is informed not until the drug is presumably lasting less than 12 hours. In reality the patient will be informed at a time point when the adjusted amount matches the first threshold value of 24 hours remaining time.

As mentioned above, block 404 is an optional block. However, in case block 404 is used, after block 422 the method does not continue with block 406 but with block 404. Block 404 relates to the possibility to dynamically adjust the first value 114 and/or the second value 116. This adjustment may consider the amount of time a patient may need to obtain additional drug for replenishment of the reservoir. For example, in case the patient is currently located in a big city, it is rather easy for the patient to go to the next pharmacy and get additional drugs for replenishment of the reservoir. In contrast, in case the patient is located in an area in which the density of pharmacies is rather low, it may be rather difficult for the patient to obtain a drug for replenishment of the reservoir in due time, especially within the time limit that he may have indicated using the first and second threshold values.

Figure 2:
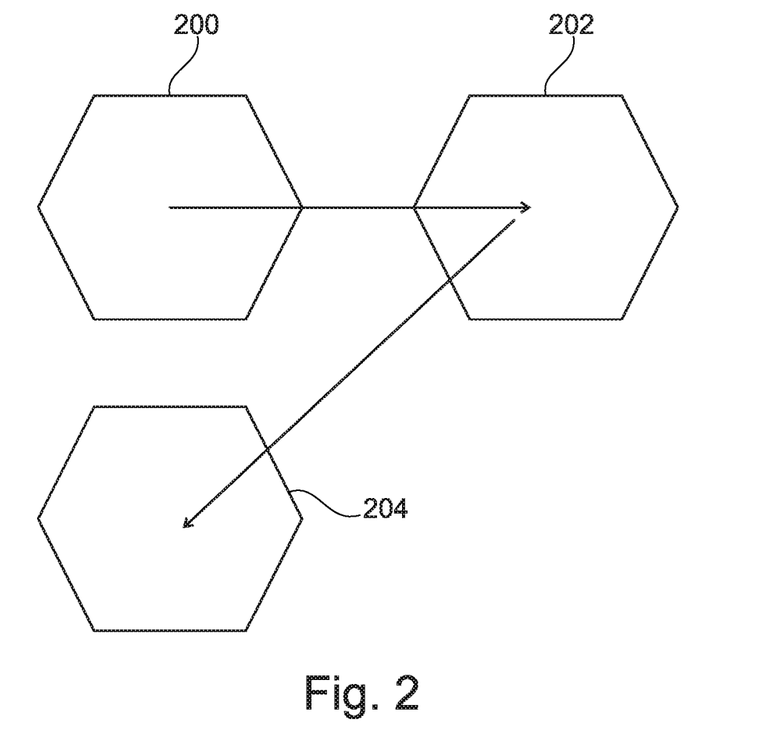
FIG. 2 is a schematic of different locations of the patient of the drug delivery system.

This is reflected in FIG. 2 which shows various locations 200, 202 and 204 of the patient of the device 100. When the patient is located at location 200, the location is detected for example via a GPS sensor 108 of the device 100 and the first and second threshold values are accordingly adjusted to that location 200. When the patient moves from location 200 to location 202, as well when the patient moves from location 202 to location 204, then a readjustment of these values is automatically performed by the insulin delivery device 100. The device 100 may either retrieve the information required to perform the adjustment from an external database or from a database comprised in the device 100. In either case, the location is used as an argument for requesting the information. The external database may be comprised in the mobile phone 132 of the patient as an app. This app may automatically retrieve the database on a regular basis from a central server, for example on a daily or monthly basis.

Instead of using the actual spatial location of the patient it may be preferable to predict the locations where the patient will be in future. For that purpose, the device 100 may for example access a calendar stored in a mobile phone 132 of the patient and extract from the calendar the future locations that the patient intends to visit according to his calendar. Another possibility is that the device 100 performs a retrospective analysis with clustering of reoccurring visits of locations by the patient according to same time periods.

For example, the device may know from historical data that each Monday the patient will be at location 200, each Tuesday the patient will be at location 202 and each Wednesday, the patient will be at location 204. Thus, the device will be able to accurately adjust the first and second threshold values since with high probability in specific future time periods the patient will again visit the same locations.

In case in block 404 it was determined, that an adjustment of the criteria is necessary, the adjustment is then performed in block 408 and the method continues again with block 406.

In block 406, irrespective of the decision block 404 and adjustment block 408, the determination of the amount of available drug may be performed in various ways: the 'remaining time period of use until the drug is used up' strongly depends on the bolus doses of the drug required by the patient in the future. Thus, the determining of the amount of available drug in block 406 may also comprise an estimation of either future bolus doses of the drug required by the patient or an estimated future physical behavior of the patient which in turn allows estimating the respectively required future bolus doses. Again, a retrospective analysis may be employed here.

Figure 3:
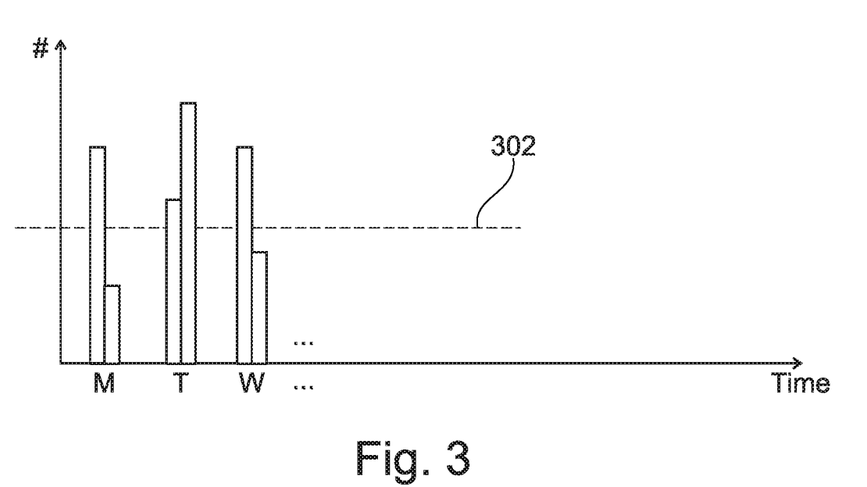
FIG. 3 is a diagram illustrating the clustering of reoccurring physical events and/or boluses according to the same time periods.

For example, in case the physical behavior of the patient like habits of eating meals at certain time points, physical activity like sports or sleeping at certain time points or time periods is considered, these habits may be retrospectively analyzed by clustering of the reoccurring of the physical events according to the same time periods. This is illustrated in the diagram of FIG. 3 which on the x-axis illustrates different days of a week (Monday, Tuesday, Wednesday . . . ) and on the y-axis shows the result of the retrospective analysis how often a certain physical behavior of the patient occurred during said day. For the sake of simplicity, only two events of physical activity are shown per day. In reality, there will be many more events than just two events per day.

The device 100 may consider all events that occurred more than n times during the last m weeks. The amount of n times is indicated by the threshold line 302 in FIG. 3, such that in the above example for Monday and Wednesday only two events are considered for the calculation of future bolus doses, whereas on Tuesday two events are considered. In turn, each event may be assigned to a certain bolus dose. In case the drug is insulin, activities like eating or doing sports or sleeping strongly influence the amount of insulin that may be required by the patient of the device 100. Thus, by considering the clustered reoccurred past physical events according to the same time periods, it may be possible to accurately determine how long the drug currently available in the reservoir will last until it is used up. On a Monday morning, step 406 may thus consider that within the next 48 hours at least three known events will again take place.

For example, the very left bar in FIG. 3 may correspond to a sports activity of a patient that in turn requires a certain high insulin bolus dose to be supplied via the device 100. While in average the currently available amount of insulin drug in the reservoir may last for the next 56 hours, the additional consideration of the high bolus dose for this sports activity may lead to an adjustment of this estimation such that the result of step 406 is that the currently available amount of insulin drug in the reservoir may last only for the next 42 hours.

It is clear that even though above only two threshold values were described, the principles described above may be extended to more than two threshold values. For example, in a scenario at 40% filling level (first threshold value) the patient is informed about a possible depletion of the reservoir within the next 2 days. At 20% filling level (second threshold value) a further information is provided to the patient in that he has to obtain and refill the drug today.

At a filling level of 10% (reserve threshold level) a signal may be provided in that the drug is to be refilled within the next 2 hours. Optionally, the caregiver may be informed. At a filling level of 5% an acoustic permanent alarm may be provided by the device 100.

LIST OF REFERENCE NUMERALS

100 insulin delivery device
101 user interface
102 reservoir
104 pump
106 infusion set
108 GBS sensor
109 controller
110 processor
112 memory
114 first value
116 second value
118 reserve value
120 address
122 instructions
124 internet
126 store
128 replacement reservoir
130 user device
132 mobile phone
200 location
202 location
204 location
302 threshold

The invention claimed is:

1. A drug delivery system for a patient comprising an insulin delivery device, a user interface, and a controller, the controller comprising instructions and a user definable threshold criterion of a residual availability of a drug provided in a reservoir of the drug delivery system, wherein the drug is insulin,
   wherein executing of the instructions by the controller causes the controller to control the drug delivery system to
   a. determine an amount of the drug that is stored outside the reservoir at the patient and that has been electronically assigned to the drug delivery system,
   b. compare the determined amount with the threshold criterion, and
   c. in response to the comparison, in case the determined amount is lower than or equal to the threshold criterion, providing a signal to the patient via the user interface, and
   wherein executing of the instructions by the controller further causes the controller to control the drug delivery system to dynamically adjust the threshold criterion based on a future location where the patient will be located in a future time period,
   the dynamical adjustment taking into account a spatial availability of the drug at said future location for replenishment of the reservoir.

2. The drug delivery system of claim 1, wherein executing of the instructions by the controller further causes the controller to control the drug delivery system to determine an amount of the drug that is currently available to the patient.

3. The drug delivery system of claim 1, the residual availability of the drug in the reservoir and/or an amount of the drug that is currently available in the reservoir being specified using any one measurement unit of
- a remaining time period of use until the drug is used up,
- a remaining amount of individual boluses until the drug is used up,
- a remaining absolute amount of the drug, and
- a remaining relative amount of the drug in relation to an amount of the drug that is maximally available in the reservoir.

4. The drug delivery system of claim 3, the remaining time period of use and/or the remaining amount of individual boluses until the drug that is currently available in the reservoir is used up being determined based on any one of
- an estimated future physical behavior of the patient,
- an estimated future carbohydrate consumption of the patient,
- estimated future bolus doses of the drug required by the patient,
- an average bolus dose of the drug per time period,
- a blood glucose measurement pattern obtained for a time period immediately preceding the time point for which the currently available amount of drug is determined,
- a remaining time period of guaranteed stability of the drug.

5. The drug delivery system of claim 1, wherein executing of the instructions by the controller further causes the controller to control the drug delivery system to dynamically adjust the threshold criterion based on
- a current location of the patient.

6. The drug delivery system of claim 1, the user interface being any one of the following:
- a graphical user interface,
- an acoustical interface,
- a haptic interface, or
- an over the air interface.

7. The drug delivery system of claim 1, the user definable threshold criterion comprising a first threshold value and a second threshold value, wherein the comparison of the determined amount with the threshold criterion is made by comparing the determined amount with the first threshold value, wherein executing of the instructions by the controller causes the controller to control the drug delivery system to
- detect in response to the provision of the signal to the patient via the user interface, the reception of a snooze command from the patient,
- in response to the detection of the reception of the snooze command, repeating steps a)-c) with the user definable threshold criterion, wherein the comparison of the determined amount with the threshold criterion for the repeating of steps a)-c) is made by comparing the determined amount with the second threshold value.

8. The drug delivery system of claim 1, the controller or a memory further comprising a user non-adjustable reserve threshold value, wherein executing of the instructions by the controller further causes the controller to control the drug delivery system to provide the signal as a dedicated warning signal to the patient via the user interface in case the determined amount is lower than or equal to the reserve threshold value.

9. The drug delivery system of claim 8, wherein executing of the instructions by the controller further causes the controller to control the drug delivery system to deactivate the dedicated warning signal upon detection of the drug in the reservoir above a minimum reservoir level.

10. The drug delivery system of claim 1, wherein the insulin delivery device is a pump delivery device comprising a pump.

11. The drug delivery system of claim 1, wherein the insulin delivery device is an insulin pen.

12. A controller for use in a drug delivery system, the controller comprising instructions and a user definable threshold criterion of a residual availability of a drug provided in a reservoir of the drug delivery system,
wherein the drug is insulin, wherein executing of the instructions by the controller causes the controller to control the drug delivery system to
  a. determine an amount of the drug that is stored outside the reservoir at a patient and that has been electronically assigned to the drug delivery system,
  b. compare the determined amount with the threshold criterion, and
  c. in response to the comparison, in case the determined amount is lower than or equal to the threshold criterion, providing a signal to the patient via a user interface of the drug delivery system, and
wherein executing of the instructions by the controller further causes the controller to control the drug delivery system to dynamically adjust the threshold criterion based on a future location where the patient will be located in a future time period, the dynamical adjustment taking into account a spatial availability of the drug at said future location for replenishment of the reservoir.

13. A method for operating a drug delivery system comprising an insulin delivery device, a user interface and a controller comprising instructions and a threshold criterion of a residual availability of a drug provided in a reservoir of the drug delivery system, wherein the drug is insulin, the threshold criterion being definable by a patient of the drug delivery device, the method comprising by the drug delivery system
  a. determining an amount of the drug that is stored outside the reservoir at the patient and that has been electronically assigned to the drug delivery system,
  b. comparing the determined amount with the threshold criterion, and
  c. in response to the comparison, in case the determined amount is lower than or equal to the threshold criterion, providing a signal to the patient via the user interface,
wherein executing of the instructions by the controller further causes the controller to control the drug delivery system to dynamically adjust the threshold criterion based on a future location where the patient will be located in a future time period, the dynamical adjustment taking into account a spatial availability of the drug at said future location for replenishment of the reservoir.

14. A computer program product comprising computer executable instructions to perform the method of claim 13.

15. A drug delivery system for a patient comprising an insulin delivery device, a user interface, and a controller, the controller comprising instructions and a user definable threshold criterion of a residual availability of a drug provided in a reservoir of the drug delivery system, wherein the drug is insulin,
wherein executing of the instructions by the controller causes the controller to control the drug delivery system to
  a. determine an amount of the drug that is currently available to the patient,
  b. compare the determined amount with the threshold criterion, and c. in response to the comparison, in case the determined amount is lower than or equal to the threshold criterion, providing a signal to the patient via the user interface, the residual availability of the drug in the reservoir and/or an amount of the drug that is currently available in the reservoir being specified using any one measurement unit of a remaining time period of use until the drug is used up, and a remaining amount of individual boluses until the drug is used up, and wherein executing of the instructions by the controller further causes the controller to control the drug delivery system to dynamically adjust the threshold criterion based on a future location where the patient will be located in a future time period, the dynamical adjustment taking into account a spatial availability of the drug at said future location for replenishment of the reservoir.

16. A drug delivery system for a patient comprising an insulin delivery device, a user interface, and a controller, the controller comprising instructions and a user definable threshold criterion of a residual availability of a drug provided in a reservoir of the drug delivery system, wherein the drug is insulin, wherein executing of the instructions by the controller causes the controller to control the drug delivery system to a. determine an amount of the drug that is currently available to the patient, b. compare the determined amount with the threshold criterion, and c. in response to the comparison, in case the determined amount is lower than or equal to the threshold criterion, providing a signal to the patient via the user interface, wherein executing of the instructions by the controller further causes the controller to control the drug delivery system to dynamically adjust the threshold criterion based on a future location where the patient will be located in a future time period, the dynamical adjustment taking into account a spatial availability of the drug at said future location for replenishment of the reservoir.

* * * * *